United States Patent
Quinn et al.

(10) Patent No.: US 6,315,968 B1
(45) Date of Patent: Nov. 13, 2001

(54) PROCESS FOR SEPARATING ACID GASES FROM GASEOUS MIXTURES UTILIZING COMPOSITE MEMBRANES FORMED FROM SALT-POLYMER BLENDS

(75) Inventors: Robert Quinn, East Texas; Daniel Vincent Laciak; Guido Peter Pez, both of Allentown, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 08/374,462

(22) Filed: Jan. 18, 1995

(51) Int. Cl.$^7$ ................. B01J 8/00; B01J 15/00
(52) U.S. Cl. ............... 423/220; 423/230; 423/239.1; 423/242.2; 423/244.07
(58) Field of Search .............. 423/210.5, 220, 423/230, 239.1, 242.2, 244.07; 95/47, 49, 51

(56) References Cited

U.S. PATENT DOCUMENTS

| | | | |
|---|---|---|---|
| 4,117,079 | * 9/1978 | Bellows | 95/51 |
| 4,119,408 | * 10/1978 | Matson | 423/220 |
| 4,174,374 | * 11/1979 | Matson | 423/220 |
| 4,500,667 | 2/1985 | Polak et al. | 524/406 |
| 4,617,029 | * 10/1986 | Pez | 423/210.5 |
| 4,761,164 | * 8/1988 | Pez et al. | 423/226 |
| 4,780,114 | 10/1988 | Quinn et al. | 55/16 |
| 4,913,818 | 4/1990 | Van Wijk et al. | 210/500.27 |
| 4,973,456 | 11/1990 | Quinn et al. | 423/210.5 |
| 5,062,866 | 11/1991 | Ho | 55/16 |
| 5,336,298 | 8/1994 | Quinn et al. | 95/49 |
| 5,445,669 | * 8/1995 | Nakabayashi et al. | 95/51 |

OTHER PUBLICATIONS

Jansen and coworkers, (Proc. Int. Conf. Pervaporation Processes Chem. Ind., 3rd, 338–341, 1988).

* cited by examiner

*Primary Examiner*—Steven P. Griffin
(74) *Attorney, Agent, or Firm*—Keith D. Gourley

(57) ABSTRACT

The present invention is a process for separating acid gas from gaseous mixtures containing acid gas and at least one non-acid gas. The process comprises bringing the gas stream into contact with a multilayer composite membrane comprising a non-selective polymeric support layer and a separating layer comprising a blend of a water soluble polymer and one-half equivalent or more of an acid gas reactive salt based upon the repeating unit of the water soluble polymer, the acid gas reactive salt which is formed from a monovalent cation and an anion for which the $pK_a$ of the conjugate acid is greater than 3, wherein the multilayer composite membrane separates the acid gas from the gaseous mixture by selectively permeating the acid gas.

23 Claims, No Drawings

PROCESS FOR SEPARATING ACID GASES FROM GASEOUS MIXTURES UTILIZING COMPOSITE MEMBRANES FORMED FROM SALT-POLYMER BLENDS

FIELD OF THE INVENTION

The present invention is a membrane-based process for removing acid gases from gaseous mixtures containing one or more acid gases and at least one non-acid gas. A general embodiment of the composite membrane comprises a microporous polymer support layer and a contiguous separating layer formed from a blend of a water-soluble polymer and one-half equivalent or more of an acid gas reactive salt based upon the repeating unit of the water soluble polymer.

BACKGROUND OF THE INVENTION

Numerous industrial processes require separating one or more acid gases such as $CO_2$ and $H_2S$ from gaseous mixtures containing such acid gases and additional non-acid gas components such as $CH_4$ and $H_2$. Such processes include separating carbon dioxide from hydrogen gas in hydrogen synthesis plants and removing $H_2S$ and $CO_2$ during the cleanup of natural gas. Numerous types of membranes have been evaluated for use in such processes taking into account economic and energy consumption considerations.

Preferred membranes for separating acid gases from gaseous mixtures are those which permeate the desired acid gases at a preferential rate over non-acid gas components such as hydrogen gas and methane in the process stream to be treated and which are highly permeable with respect to such acid gases. However, such membranes are relatively rare and sometimes have limited utility because the membranes exhibit insufficient acid gas permeability.

U.S. Pat. No. 4,500,667 discloses gas separation membranes comprising an organic polymer-inorganic compound blend which is prepared by admixing an organic polymer such as poly(vinyl alcohol) with a heteropoly acid or salt thereof such as dodecamolybdophosphoric acid in a mutually miscible solvent. After allowing the mixture to react for a period of time sufficient to form a blend, the solution is cast on an appropriate casting surface, the solvent is evaporated and the desired membrane is recovered. The membranes are suitable for separating water from a water-containing hydrogen stream.

U.S. Pat. No. 4,780,114 discloses membranes which selectively permeate acid gases such as $CO_2$ or $H_2S$ over non-acid gas components. The membranes comprise a thin film of a molten salt hydrate which may be immobilized within the pores of a thin, porous inert support or alternatively, may be encapsulated in a non-porous, gas permeable polymer such as poly(trimethylsilylpropyne), polymer blends or silicone rubber. The term, molten salt hydrate, refers to a salt, which upon heating, melts to yield a liquid system which contains bound water. Molten salt hydrates are represented by the formula $A_xB_y \cdot nH_2O$ wherein A and B are ionic species of opposite charge and n represents the number of moles of bound water per mole of salt. Representative molten salt hydrates include tetramethylammonium fluoride tetrahydrate and tetramethylammonium acetate tetrahydrate.

U.S. Pat. No. 4,913,818 discloses a process for removing water vapor from a gas/vapor mixture such as a water-alcohol mixture, which utilizes a regenerated cellulose membrane which is impregnated with a hygroscopic electrolyte salt. The electrolyte is desirably a salt of an alkali metal, an alkaline earth metal or a transition metal wherein the anion is a chloride, bromide, fluoride, sulphate or nitrate. Representative salts include LiBr, KCl, $MgCl_2$, $CaCl_2$, $SrSO_4$ and $NaNO_3$. A cellulose membrane impregnated with LiBr provided a 2.5-fold increase in water vapor flux over the same cellulose membrane containing no salt.

Jansen and coworkers, (Proc. Int. Conf. Pervaporation Processes Chem. Ind., 3rd, 338–341, 1988) disclose cellulose and poly(vinyl alcohol) (PVOH) membranes which are impregnated with CsF. The CsF-impregnated PVOH membrane provided an approximate doubling of water vapor flux although water/alcohol selectivity decreased by an unspecified amount. Higher water vapor fluxes were obtained by repeatedly impregnating the membrane with CsF. The reference does not teach or suggest that the disclosed membranes permeate carbon dioxide.

U.S. Pat. No. 4,973,456 discloses a process for reversibly absorbing acid gases such as $CO_2$, $H_2S$, $SO_2$ and HCN present in a gaseous mixture wherein the gaseous mixture is contacted with a hydrate salt represented by the formula $A_x^{m+}B_y^{n-} \cdot rH_2O$ wherein $A^{m+}$ is a cation, $B^{n-}$ is the conjugate base of a weak acid having a $pK_a$ corresponding to an ionization constant of the acid greater than 3 as measured in dilute aqueous solution, m and n are independently selected integers from 1–4, x and y are integers such that the ratio of x to y provides a neutral salt and r is any number greater than zero up to the maximum number of moles of water which can be bound to the salt. Representative salt hydrates include tetramethylammonium fluoride tetrahydrate, tetramethylammonium acetate tetrahydrate and cesium fluoride.

U.S. Pat. No. 5,062,866 discloses a process for separating an unsaturated hydrocarbon from a feed stream containing such unsaturated hydrocarbon wherein the feed stream is contacted with a membrane comprising a blend of hydrophilic polymer and a hydrophilic alkali metal salt and metals which are reactive with respect to the desired unsaturated hydrocarbon. Suitable polymers include polyvinyl alcohol, polyvinyl acetate, sulfonyl-containing polymers polyvinylpyrrolidone and the like. Suitable metal salts include silver nitrate.

U.S. Pat. No. 5,336,298, assigned to Air Products and Chemicals, Inc., Allentown, Pa., teaches a process for separating acid gases from a gaseous mixture containing acid gas and at least one non-acid gas component wherein the gaseous mixture is brought into contact with a multilayer composite membrane comprising an essentially non-selective polymeric support layer and a separating layer comprising a polyelectrolyte polymer which contains cationic groups which are electrostatically associated with anions for which the $pK_a$ of the conjugate acid is greater than 3. The multilayer composite membrane selectively permeates acid gas thereby removing the same from the gaseous mixture. Suitable polyelectrolyte polymers include poly(diallyldimethylammonium fluoride), poly (diallyldimethylammonium acetate), poly (vinylbenzyltrimethylammonium fluoride) and poly (vinylbenzylammonium acetate).

Industry is searching for improved membranes for separating acid gases from acid-gas containing gaseous mixtures wherein the membrane would desirably exhibit substantially improved permeability to the acid gas to be separated from the feedstream without sacrificing selectivity for the component to be passed through the membrane.

SUMMARY OF THE INVENTION

The present invention relates to a process for selectively removing acid gases from a gaseous mixture containing such acid gases. The process utilizes a composite membrane comprising a non-selective polymeric support layer and a separating layer which comprises a blend of a water soluble polymer and one-half equivalent or more of at least one acid gas reactive salt based upon the repeating unit of the water soluble polymer, each acid gas reactive salt comprising a monovalent cation and an anion for which the $pK_a$ of the conjugate acid is greater than 3. Suitable acid gas reactive salts can be represented by the formula $A_xB_y \cdot nH_2O$ wherein A and B are ionic species of opposite charge and n is the number of moles of bound water per mole of salt and x and y are integers such that the salt remains charge neutral. While "n" presented in the formula must be a number greater than 1 and is bounded by the maximum number of moles of water which can be bound to the salt, the membranes of the present invention may be installed for operation when "n" equals zero provided the gaseous mixture to be treated contains water vapor in an amount sufficient to hydrate the acid gas reactive salt. Optionally, a third layer referred to as a protective layer, may be deposited onto the active separating layer to provide added strength and resistance to abrasion.

The membranes of the present process are unique compared to conventional polymeric membranes because they selectively permeate $CO_2$, $H_2S$ and other acid gases while retaining non-acid gases such as $H_2$ and $CH_4$ at feed pressure. Thus, contaminant acid gases can be removed from a feedstream while maintaining the bulk components of the feedstream at pressure. The present process accomplishes this result because acidic gases can react with the acid gas reactive salt and/or the water soluble polymer of the separating layer of the membrane in a manner which enhances acid gas permeation. In contrast, non-acid gases such as $H_2$ and $CH_4$ can only permeate through the membrane by physically dissolving and diffusing across the membrane. Since the membrane is highly ionic, solubilities of $H_2$ and $CH_4$ are very low, permeance is minimized and the separating layer serves essentially as a barrier to the non-acid gas components of the feedstream.

Representative acid gas reactive salts suitable for use in the separating layer of the membrane include cesium fluoride, tetramethylammonium fluoride, cesium acetate, cesium pipecolinate and choline fluoride. Water soluble polymers can be selected from a variety of polyelectrolytes or polymers containing polar functional groups. Particularly useful water soluble polymers include poly(vinylbenzyltrimethylammonium fluoride), poly(vinyl alcohol) and poly(vinyl amine).

Compared to prior art facilitated transport membranes wherein the salts and salt hydrates are immobilized within the pores of the supporting layer of the membrane, the acid gas reactine salts of the present invention are substantially soluble in the water soluble polymer substrate thereby reducing problems associated with hole formation which might occur in prior art membranes when feed pressure exceeds the bubble point of the substrate.

DETAILED DESCRIPTION OF THE INVENTION

The present invention is a process which uses a multilayer composite membrane for selectively removing acid gases such as $CO_2$, $H_2S$, $COS$, $SO_2$ and $NO_x$ from gas mixtures while retaining non-acid gases such as $H_2$, $CH_4$, $N_2$, $O_2$ and $CO$, at pressure in the feed stream contacting the membrane. The membranes used in this process comprise a minimum of two layers, and more typically three or more layers, at least one of which consists of a separating layer comprising a blend of a water soluble polymer, typically a polyelectrolyte or a polymer containing polar function groups, and one-half equivalent or more of at least one acid gas reactive salt, the number of equivalents being based upon the repeating unit of the water soluble polymer. Suitable acid gas reactive salts can be represented by the formula $A_xB_y \cdot nH_2O$ wherein A and B are ionic species of opposite charge and n is the number of moles of bound water per mole of salt and x and y are integers such that the salt remains charge neutral. While "n" presented in the formula must be a number greater than 1 and is bounded by the maximum number of moles of water which can be bound to the salt, the membranes of the present invention may be installed for operation when "n" equals zero provided the gaseous mixture to be treated contains water vapor in an amount sufficient to hydrate the acid gas reactive salt.

In the most general embodiment of the invention, the process for separating acid gases from a gaseous mixture containing acid gas and at least one non-acid gas comprises contacting the gaseous mixture with a multilayer composite membrane comprising a first polymeric support layer and a separating layer comprising a blend of a water soluble polymer and one-half equivalent or more of at least one acid gas reactive salt based upon the repeating unit of the water soluble polymer, the acid gas reactive salt which is formed from a monovalent cation and an anion for which the $pK_a$ of the conjugate acid is greater than 3, wherein the multilayer composite membrane separates the acid gases from the gaseous mixture by selectively permeating the acid gases. Suitable acid gas reactive salts can be represented by the formula $A_xB_y \cdot nH_2O$ wherein A and B are ionic species of opposite charge and n is the number of moles of bound water per mole of salt and x and y are integers such that the salt remains charge neutral. The composite membranes may be used in any configuration known in the art, such as flat sheets, spiral wound, hollow fiber, plate and frame as conventionally known in the art, and the like.

The membranes of the present process are particularly useful for separating $CO_2$ from $CH_4$ and $H_2$, and $H_2S$ from $CH_4$ and $H_2$. The process comprises contacting a gaseous feed stream containing one or more acid gases and at least one non-acid component with the feed side of the membrane and recovering a gas stream which is enriched with the desired acid gas at the permeate side of the membrane. The permeate gases may be collected directly or alternately, their recovery may be facilitated by sweeping the permeate side of the membrane with an inert gas or the acid gas being collected. Suitable sweep gases include inert gases such as nitrogen, helium and argon. However, the process can be operated without using a sweep gas.

In most cases, the composite membranes are effectively operated by maintaining a minimal partial vapor pressure difference of water between the feed stream and permeate sweep) streams to the membrane in order to retain the activity of the acid gas reactive salt toward transporting acid gases across the composite membrane.

The composite membranes of the present process are unique relative to typical polymeric membranes in that they are substantially impermeable to non-acid gases such as $H_2$ and $CH_4$ while they are highly permeable toward acid gases. Typically, $H_2$ can permeate conventional polymeric membranes at a rate comparable to or greater than $CO_2$ and $H_2S$. Thus, $CO_2$ to $H_2$ and $H_2S$ to $H_2$ selectivities for conventional polymeric membranes are relatively small and usually less than one. In contrast, the multilayer composite membranes of the present invention exhibit relatively high $CO_2$ to $H_2$ and H₂S to H₂ selectivities. Consequently, the membranes of the present process permit the application of membrane technology to separations which were unachieveable using conventional polymeric membranes.

In an alternate embodiment of the process, the multilayer composite membrane comprises a third layer, referred to as a protective layer, which is deposited onto the separating layer to provide the membrane with added strength and resistance to abrasion and the like. Suitable protective films are selected from dense permeable polymer films such as poly(dimethylsiloxane) (PDMS) and poly (trimethylsilylpropyne) (PTMSP).

The membranes of the present invention exhibit gas permeance rates which are dependent upon the acid gas partial pressure of the gaseous mixture to be separated. For example, the data shall demonstrate that $CO_2$ permeance of the subject composite membranes increases with decreasing $CO_2$ feed partial pressure which is consistent with facilitated transport of $CO_2$ and implies chemical reactivity of $CO_2$, an acid gas, with the separating layer. The chemical reactivity of the acid gas components of the gaseous mixture to be separated with the acid gas reactive salt blended in the water soluble polymer of the active separating layer results in relatively high acid gas permeances while desirably limiting permeance of the non-acid gas components. Moreover, the acid gas components may exhibit chemical reactivity with the separating layer when formed from a polyelectrolyte. For purposes of this invention, the term, facilitated transport, refers to an acid gas transfer mechanism wherein the acid gases to be separated from the gaseous mixture are capable of reacting with one or both components of the separating layer of the membrane.

The microporous polymer support layer of the composite membrane is highly permeable but typically non-selective and serves principally to support the active separating layer. The support layer can be fabricated from a wide variety of materials including dense materials such as poly (dimethylsiloxane) and poly(trimethylsilyl propyne) or microporous materials such as polysulfones or conventional ceramics. The microporous layer can be fabricated in any conventional manner including flat sheets or hollow fiber configurations. Such polymeric materials optionally may have asymmetrically distributed pore sizes.

The separating layer of the multilayer composite membrane comprises a blend of two components. The first component is a water soluble polymer which may be a polyelectrolyte or a polymer containing polar functional groups. The second component is an acid gas reactive salt comprising a monovalent cation and an anion for which the $pK_a$ of the conjugate acid is greater than 3. Suitable acid gas reactive salts can be represented by the formula $A_xB_y \cdot nH_2O$ wherein A and B are ionic species of opposite charge and n is the number of moles of bound water per mole of salt and x and y are integers such that the salt remains charge neutral. The term, blend, means that the recited components are thoroughly mixed whereby the acid gas reactive salt is dispersed throughout the water soluble polymer or polyelectrolyte. This blend can be a true solution in which the salt is solubilized in the polymer or the blend can be a mixture where two distinct phases are present and the salt is dispersed in the polymer. Applicants have discovered that the membranes of the present process are not adversely affected if a minor amount of salt crystallizes out the blend. Therefore, the practitioner need not be concerned with adding too much salt to the water soluble polymer such that the blend becomes saturated with salt.

The term, water soluble polymers, means polymers which are soluble in water or which are dispersible in water. Such materials can be summarized in two categories, polyelectrolytes and polymers containing polar functional groups. The water soluble polymer should preferably exhibit low permeance of the non-acid gas components of the gaseous mixture to be separated.

Examples of suitable water soluble polymers include polyelectrolytes such as poly(diallyldimethylammonium fluoride) (PDADMAF), poly (vinylbenzyltrimethylammonium fluoride) (PVBTAF), poly (vinylbenzyltrimethylammonium chloride) (PVBTCl), poly (diallyldimethylammonium acetate) (PDADMAOAc), poly (vinylbenzyltrimethylammonium acetate) (PVBTAOAc), poly(vinyl N-methylpyridinium fluoride), poly(vinyl N-methylpyridinium acetate), poly(vinyl N,N-dimethylimidazolium fluoride), poly(vinyl N,N-dimethylimidazolium acetate), poly(N,N-dimethylethyleneimine fluoride), poly(N,N-dimethylethyleneimine acetate), poly(2-hydroxypropyl dimethylammonium fluoride), poly(2-hydroxypropyl dimethylammonium acetate), and the like. The molecular weight of the water soluble polymer is not believed to be critical and the polymer need only have a molecular weight sufficient to cast suitable films.

Polyelectrolytes as used herein are distinguishable from substantially water-insoluble ionic polymers and ion-exchange polymers in that polyelectrolytes have a relatively high ionic content, i.e., up to one ionic unit per polymer repeat unit. Ionic polymers, on the other hand, are compounds possessing organic or inorganic salt groups which are attached to a polymer chain and which have relatively low ionic content, usually less than 10 mole % with respect to the polymer chain repeat unit. Ion exchange polymers generally consist of an insoluble polymer matrix or resin to which are attached ionizable functional groups. Cation exchange resins have a fixed negative charge on the polymer matrix with exchangeable cations (and vice-versa for anion-exchange resins).

Preferably, the water soluble polymer reversibly reacts with the acid gas in the presence of water vapor. However, such reactivity is not required in order for the membranes to provide the benefits discussed in this Specification. For example, polyelectrolytes which contain non-reactive anions, such as Cl⁻ in PVBTACl, exhibits low gas permeance and non-facilitated transport of acid gases as evidenced by the independence of acid gas permeance on feed partial pressure. However, significantly higher permeances and selectivities are obtained when an acid gas reactive salt is blended with such non-reactive water soluble polymers wherein the resulting salt/polymer blends exhibit facilitated transport of acid gases as demonstrated by the relationship between permeance and feed partial pressure. Moreover, amino acid salts such as cesiumn pipecolinate which are more reactive with respect to $H_2S$ over $CO_2$ can be used to fabricate membranes which selectively permeate $H_2S$ over $CO_2$.

Other polymers which are not polyelectrolytes but contain polar functional groups can be used in conjunction with appropriate acid gas reactive salts to fabricate the active separating layer of the composite membranes. Suitable water soluble polymers which contain polar functional groups include poly(vinyl alcohol) (PVOH), poly (vinylamine) (PVAm) and carbonyl-containing polymers such as polyvinylpyrrolidone. While membranes formed from these materials are essentially unreactive with respect to acid gases and exhibit relatively low gas permeance, unexpectedly superior acid gas permeability and selectivity is achieved by adding the enumerated acid gas reactive salts to these polymers.

The separating layer of these composite membranes further comprises an acid gas reactive salt which is blended with the water soluble polymer. The acid gas reactive salt contains cationic groups which are associated electrostatically with anions for which the $pK_a$ of the conjugate acid is greater than 3. The value of the $pK_a$ is that obtained for the conjugate acid as determined in a dilute aqueous solution. Examples of suitable anions include $F^-$ ($pK_a$ HF=3.45) and the acetate ion ($pK_a$ acetic acid=4.75). Preferred salts are those which contain fluoride, acetate or carboxylate anions.

Suitable acid gas reactive salts can be represented by the formula $A_xB_y \cdot nH_2O$ wherein A and B are ionic species of opposite charge and n is the number of moles of bound water per mole of salt and x and y are integers such that the salt remain charge neutral. Suitable salts include those which react reversibly with acid gases, in particular $CO_2$ and $H_2S$. Such reactive salts consist of monovalent cations and anions for which the $pK_a$ of the conjugate acid of the anion is greater than 3. Representative salts include cesium fluoride, tetramethylammonium fluoride, cesium acetate and choline fluoride. Additionally, amino acid salts such as cesium pipecolinate which are more reactive with respect to $H_2S$ than $CO_2$ can be used to fabricate membranes which selectively permeate $H_2S$ over $CO_2$.

The concentration of acid gas reactive salt to be added to the water soluble polymer can be varied to alter the permselective properties of the composite membrane. As the quantity of added gas reactive salt to be blended with the water soluble polymer is increased, acid gas permeance for the membrane increases without substantial loss of selectivity.

The following examples are presented to better illustrate the present invention and are not meant to be limiting.

Experimental

Membranes were prepared using aqueous or methanolic casting solutions containing the desired water soluble polymer and acid gas reactive salt. In general, casting solutions were prepared by dropwise addition of an aqueous acid gas reactive salt solution with rapid stirring to a polymer solution. Casting solutions were applied to either flat sleet or hollow fiber microporous supports and dried at room temperature in a shroud which was constantly purged with $N_2$. In some cases, a protective layer of a poly (dimethylsiloxane)-like material such as Petrarch MB PS254 obtained from Huls America, Bristol, Pa. was applied using a 1–5 wt. % polymer solution in $CH_2Cl_2$.

The membrane apparatus used was similar to that described by Bateman, et al., (Sep. Sci. Tech. 19, 21–32 (1984)). The membrane was sealed in a stainless steel cell similar to that described by Otto, et al., (J. Appl. Polym. Sci. 38, 2131–2147 (1989)). The feed gas to the membrane cell was obtained from premixed gas cylinders. Either nitrogen or helium was used as a sweep gas. Generally, thermal mass flow controllers were used to maintain feed pressure and sweep gas flow rates were maintained between 10 and 20 $cm^3$(STP)/min. Feed gas pressures greater than ambient were maintained by employing a back pressure regulator.

The sweep gas pressure was atmospheric. Both the feed and sweep gases, except where indicated, were humidified by passage through constant temperature water bubblers. The feed gas was passed over one surface of the membrane and the sweep gas over the other. The sweep gas stream was then passed through the sample loop of a gas chromatograph and a sample for analysis was injected periodically. Data was collected over a minimum of 24 h. The determination of the concentration of permeating gases permitted calculation of gas flux. Permeance, $P_o/l$, in units of $cm^3$(NTP)/$cm^2 \cdot s \cdot cmHg$ was calculated using the equation below:

$$P_o/l = J/A\Delta P$$

where J represents gas flow in $cm^3$(NTP)/s, A is the membrane area in $cm^2$ and $\Delta P$ is the difference in the feed and permeate partial pressures of gas in cmHg. For flat sheet membranes, A was 3.77 $cm^2$ and 3–15 $cm^2$ for hollow fiber modules. Selectivity is the ratio of permeances or permeabilities of two gases. The term equivalent (equiv) is taken as the number of moles of added salt per mole of polymer repeat unit. Unless otherwise stated, aqueous casting solutions were employed to make films of the present invention.

Because many of the membranes described in the Examples exhibited low $CH_4$ permeances, $CH_4$ was often not detected in the sweep gas. When $CH_4$ was not detected, selectivity was estimated in one of two ways as indicated in each example.

EXAMPLE 1 (COMPARATIVE) SEPARATION OF A $CO_2/CH_4/H_2$ GASEOUS MIXTURE USING A MEMBRANE FORMED FROM POLY(VINYL BENZYLTRIMETHYLAMMONIUM FLUORIDE) (PVBTAF)

A poly(vinylbenzyltrimethylammonium fluoride) (PVBTAF) membrane containing no added acid gas reactive salt was fabricated on a flat sheet microporous polysulfone support using a methanolic casting solution containing 5.0 wt. % of PVBTAF. PVBTAF was prepared by the following procedure wherein 42 g of 30% PVBTACl (obtained from Scientific Polymer Products, Inc., Ontario, N.Y.) was mixed with 155 g water. The resulting mixture was added slowly with rapid stirring to a solution of 53.4 g KF in 150 ml of water. The solution was loaded into dialysis tubing and dialyzed against three changes of deionized water. To the resulting solution was added slowly and with rapid stirring 57.1 g KF in 150 ml water. The volume of solution had become so large that about half of the water was removed Linder vacuum at 60° C. The solution was dialyzed against four changes of deionized water. The resulting solution was filtered and the solvent volume was reduced as above to about one-third of the original volume. A polymer film was prepared by placing the solution under flowing nitrogen for an extended period of time. Permselective data was obtained as a function of feed pressure under the conditions listed below.

PVBTAF flat sheet membrane at 23° C.; feed: 30.6% $CO_2$, 34.4% $CH_4$ in $H_2$; $N_2$ sweep; 5° C. feed and sweep water bubblers.

| feed | $CO_2$ | $(P_o/l) \cdot 10^6$ cc/$cm^2 \cdot s \cdot cmHg$ | | | selectivity | |
|---|---|---|---|---|---|---|
| P(psig) | P(cmHg) | $CO_2$ | $H_2$ | $CH_4$ | $CO_2/H_2$ | $CO_2/CH_4$ |
| 5.3 | 31.6 | 6.02 | 0.0602 | nd | 87 | 1000[a] |
| 20.0 | 54.9 | 4.51 | 0.0548 | nd | 82 | 760[a] |
| 40.0 | 86.5 | 3.78 | 0.0536 | nd | 71 | 640[a] |
| 61.1 | 119.9 | 3.19 | 0.0662 | nd | 48 | 540[a] |
| 75.6 | 142.9 | 2.88 | 0.0676 | 0.00586 | 43 | 490 |

[a]Estimated selectivity
nd = none detected $CH_4$ was not detected in the permeate at the lower feed pressures examined. At the enumerated pressures, $CO_2/CH_4$ selectivities were estimated using an $CH_4$ permeance of 0.00586 at 75.6 psig feed pressure.

EXAMPLE 2 SEPARATION OF A $CO_2/CH_4/H_2$ GASEOUS MIXTURE USING A MEMBRANE FORMED FROM A BLEND OF PVBTAF AND 0.5 EQUIV. CESIUM FLUORIDE (CsF)

A flat sheet membrane was prepared on a microporous polysulfone support as described in Example 1 using an aqueous casting solution consisting of 4.13 wt. % PVBTAF and 0.5 equiv CsF. Permselective data was collected as a function of the feed gas pressure under the conditions listed below.

PVBTAF-0.5CsF flat sheet membrane at 23° C.; feed: 30.6% $CO_2$, 34.4% $CH_4$ in $H_2$; $N_2$ sweep; 5° C. feed and sweep water bubblers.

| feed | $CO_2$ | $(P_x/l) \cdot 10^6$ cc/cm² · s · cmHg | | | selectivity | |
|---|---|---|---|---|---|---|
| P(psig) | P(cmHg) | $CO_2$ | $H_2$ | $CH_4$ | $CO_2/H_2$ | $CO_2/CH_4$ |
| 2.8 | 27.7 | 9.94 | 0.0296 | nd | 335 | 2600[a] |
| 14.3 | 45.9 | 8.46 | 0.0290 | nd | 291 | 2200[a] |
| 25.0 | 62.9 | 7.10 | 0.0273 | 0.00413 | 260 | 1720 |
| 39.7 | 86.2 | 5.92 | 0.0249 | 0.00337 | 238 | 1760 |
| 85.9 | 159.4 | 4.30 | 0.0329 | 0.00361 | 131 | 1190 |
| 107.0 | 192.9 | 3.45 | 0.0350 | 0.00399 | 99 | 866 |

[a]Estimated selectivities
nd = none detected

The observed increase in $CO_2$ permeance with decreasing feed partial pressure of $CO_2$ is consistent with facilitated transport of $CO_2$. In contrast, permeances of $CH_4$ and $H_2$ were relatively constant implying facilitated transport by a solution diffusion pathway. $CH_4$ was not detected in the permeate at the lower feed pressures examined. At the enumerated pressures, $CO_2/CH_4$ selectivities were estimated using an average observed $CH_4$ permeance of 0.0038. A comparison of the data presented in this Example and the data of Example 1 illustrates the improvement in membrane performance obtained by adding CsF into the water-soluble polymer component of the separating layer. At comparable feed pressures, $CO_2/H_2$ and $CO_2/CH_4$ selectivities are at least doubled and $CO_2$ permeances are somewhat higher as well.

EXAMPLE 3 SEPARATION OF A $CO_2/CH_4/H_2$ GASEOUS MIXTURE USING A MEMBRANE FORMED FROM A BLEND OF PVBTAF AND 1.1 EQUIV. CsF

A flat sheet membrane was prepared on a microporous polysulfone support using an aqueous casting solution consisting of 3.98 wt. % PVBTAF and 1.1 equiv CsF. Permselective data was collected as a function of the feed gas pressure under the conditions listed below.

PVBTAF-1.1CsF flat sheet membrane at 23° C.; feed: 30.6% $CO_2$, 34.4% $CH_4$ in $H_2$; $N_2$ sweep; 5° C. feed and sweep water bubblers.

| feed | $CO_2$ | $(P_x/l) \cdot 10^6$ cc/cm² · s · cmHg | | | selectivity | |
|---|---|---|---|---|---|---|
| P(psig) | P(cmHg) | $CO_2$ | $H_2$ | $CH_4$ | $CO_2/H_2$ | $CO_2/CH_4$ |
| 5.5 | 32.0 | 13.0 | 0.107 | nd | 122 | 2150[a] |
| 21.1 | 56.7 | 10.8 | 0.102 | nd | 106 | 1800[a] |
| 39.8 | 86.4 | 9.18 | 0.102 | 0.00864 | 90 | 1060 |
| 53.5 | 108.1 | 7.57 | 0.0888 | 0.00421 | 85 | 1800 |
| 81.0 | 151.7 | 6.05 | 0.0831 | 0.00524 | 73 | 1150 |

[a]Estimated selectivities
nd = none detected $CH_4$ was not detected in the permeate at the lower feed pressures examined. At the enumerated pressures, $CO_2/CH_4$ selectivities were estimated using an average observed $CH_4$ permeance of 0.0060. The membranes according to this Example which contain 1.1 equiv CsF provided still larger $CO_2$ permeances and selectivities comparable to those obtained using the membrane according to Example 2.

EXAMPLE 4 SEPARATION OF A $CO_2/CH_4/H_2$ GASEOUS MIXTURE USING A MEMBRANE FORMED FROM A BLEND OF PVBTAF AND 4.2 EQUIV CsF

A flat sheet membrane was prepared on a microporous polysulfone support using an aqueous casting solution consisting of 3.41 wt. % PVBTAF and 4.2 equiv CsF. Permselective data was collected as a function of the feed gas pressure under the conditions listed below.

PVBTAF-4.2CsF flat sheet membrane at 23° C.; feed: 33.1% $CO_2$, 33.1% $CH_4$ in $H_2$; $N_2$ sweep; 5° C. feed and sweep water bubblers.

| feed | $CO_2$ | $(P_x/l) \cdot 10^6$ cc/cm² · s · cmHg | | | selectivity | |
|---|---|---|---|---|---|---|
| P(psig) | P(cmHg) | $CO_2$ | $H_2$ | $CH_4$ | $CO_2/H_2$ | $CO_2/CH_4$ |
| 3.2 | 30.6 | 25.7 | 0.203 | 0.0438 | 127 | 588 |
| 15.9 | 52.4 | 24.1 | 0.228 | 0.0535 | 106 | 450 |
| 26.0 | 69.7 | 21.9 | 0.218 | 0.0469 | 100 | 466 |
| 40.0 | 93.8 | 21.5 | 0.238 | 0.0511 | 90 | 420 |
| 54.9 | 119.3 | 19.1 | 0.248 | 0.0425 | 77 | 449 |
| 94.6 | 187.4 | 13.0 | 0.299 | 0.0350 | 43 | 370 |

Compared to the PVBTAF membrane containing no salt (Example 1), the membrane in this Example provided nearly a six fold improvement in $CO_2$ permeance at comparable $CO_2$ feed partial pressure. $CO_2/H_2$ and $CO_2/CH_4$ selectivities were comparable to the performance of the membrane according to Example 1 which contained no acid gas reactive salt.

EXAMPLE 5 SEPARATION OF A $CO_2/CH_4/H_2$ GASEOUS MIXTURE USING A MEMBRANE FORMED FROM A BLEND OF PVBTAF AND 0.94 EQUIV TMAF

A flat sheet membrane was prepared on a microporous polysulfone support using a casting solution consisting of 4.12 wt. % PVBTAF and 0.94 equiv tetramethylammonium fluoride. Permselective data was collected under the conditions listed below.

PVBTAF-0.9TMAF flat sheet membrane at 23° C.; feed: 32.9% $CO_2$, 32.6% $CH_4$ in $H_2$; $N_2$ sweep; 5° C. feed and sweep water bubblers.

| feed | | $(P_o/l) \cdot 10^6$ cc/cm$^2 \cdot$ s $\cdot$ cmHg | | | selectivity | |
|---|---|---|---|---|---|---|
| P(psig) | P(cmHg) | CO$_2$ | H$_2$ | CH$_4$ | CO$_2$/H$_2$ | CO$_2$/CH$_4$ |
| 39.6 | 92.5 | 8.29 | 0.134 | 0.0171 | 62 | 484 |

The membrane of this Example provided a two fold increase in CO$_2$ permeance compared to the PVBTAF membrane of Example 1 which did not contain an acid gas reactive salt. Moreover, the addition of the acid gas reactive salt did not adversely affect membrane selectivity.

EXAMPLE 6 SEPARATION OF A CO$_2$/CH$_4$/H$_2$ GASEOUS MIXTURE USING A MEMBRANE FORMED FROM A BLEND OF PVBTAF AND 1.0 EQUIV CESIUM ACETATE (CsCH$_3$CO$_2$)

A membrane was prepared by casting a solution of 4.33% PVBTAF in water solution containing 1.0 equiv of cesium acetate (CsCH$_3$CO$_2$). The membrane was evaluated at a variety of feed pressures under the conditions listed below.

PVBTAF-CsCH$_3$CO$_2$ flat sheet membrane at 23° C.; feed: 32.9% CO$_2$, 32.6% CH$_4$ in H$_2$; N$_2$ sweep; 5° C. feed and sweep water bubblers.

| feed | | $(P_o/l) \cdot 10^6$ cc/cm$^2 \cdot$ s $\cdot$ cmHg | | | selectivity | |
|---|---|---|---|---|---|---|
| P(psig) | P(cmHg) | CO$_2$ | H$_2$ | CH$_4$ | CO$_2$/H$_2$ | CO$_2$/CH$_4$ |
| 10.2 | 42.4 | 6.61 | 0.0869 | nd | 76 | 700[a] |
| 20.4 | 59.8 | 5.84 | 0.0826 | nd | 71 | 620[a] |
| 39.6 | 92.5 | 5.46 | 0.101 | 0.00964 | 54 | 567 |
| 62.0 | 130.7 | 3.99 | 0.0825 | 0.00913 | 48 | 436 |
| 75.2 | 153.2 | 3.49 | 0.0774 | 0.0183 | 45 | 191 |

[a]Estimated selectivities
nd = none detected

As expected for a facilitated transport membrane, CO$_2$ permeance decreased with increasing feed pressure. CH$_4$ was not detected in the permeate at the lower feed pressures examined. At the enumerated pressures, CO$_2$/CH$_4$ selectivities were estimated using an average observed CH$_4$ permeance of 0.0094. A 15–20% increase in CO$_2$ permeance without selectivity loss was obtained compared to Example 1.

EXAMPLE 7 SEPARATION OF A CO$_2$/CH$_4$/H$_2$ GASEOUS MIXTURE USING A MEMBRANE FORMED FROM A BLEND OF CESIUM POLY(ACRYLATE) (CsPA) AND 1.2 EQUIV CsF

A flat sheet membrane was prepared on a microporous polysulfone support using a casting solution consisting of 3.61% cesium poly(acrylate) (CsPA) and 1.2 equiv CsF. Permselective data was collected as a function of the feed gas pressure under the conditions listed below.

CsPA-1.2 CsF flat sheet membrane at 23° C.; N$_2$ sweep; feed: 33.1% CO$_2$, 33.1% CH$_4$ in H$_2$; 5° C. water bubblers.

| feed | | $(P_o/l) \cdot 10^6$ cc/cm$^2 \cdot$ s $\cdot$ cmHg | | | selectivity | |
|---|---|---|---|---|---|---|
| P(psig) | P(cmHg) | CO$_2$ | H$_2$ | CH$_4$ | CO$_2$/H$_2$ | CO$_2$/CH$_4$ |
| 5.0 | 33.7 | 8.12 | 0.135 | nd | 60 | 450[a] |
| 20.6 | 60.5 | 7.55 | 0.123 | nd | 61 | 420[a] |
| 40.2 | 94.1 | 7.58 | 0.148 | 0.0208 | 51 | 364 |
| 61.1 | 129.9 | 6.98 | 0.128 | 0.157 | 55 | 445 |
| 98.0 | 193.2 | 6.58 | 0.129 | 0.0176 | 51 | 374 |

[a]Estimated selectivities
nd = none detected

CH$_4$ was not detected in the permeate at the lower feed pressures examined. At the enumerated pressures, CO$_2$/CH$_4$ selectivities were estimated using an average observed CH$_4$ permeance of 0.018. The results obtained in this Example are contrasted with a comparative run wherein no CsF was added to the water soluble polymer which provided no measurable permselectivity.

EXAMPLE 8 (COMPARATIVE) SEPARATION OF A CO$_2$/CH$_4$/H$_2$ GASEOUS MIXTURE USING A MEMBRANE FORMED FROM POLY(VINYLBENZYLTRIMETHYLAMMONIUM CHLORIDE) PVBTACl

A poly(vinylbenzyltrimethylammonium chloride) (PVBTACl) membrane containing no acid gas reactive salt in the separating layer was fabricated on a flat sheet of microporous polysulfone support using an aqueous 4.3 wt. % polymer casting solution. Permselective data were obtained as a function of feed pressure under the conditions listed below. The data demonstrate that the membrane provided low permeance and poor selectivity.

PVBTACl flat sheet membrane at 23° C.; feed: 32.9% CO$_2$, 32.6% CH$_4$ in H$_2$; N$_2$ sweep; 5° C. feed and sweep water bubblers.

| feed | | $(P_o/l) \cdot 10^6$ cc/cm$^2 \cdot$ s $\cdot$ cmHg | | | selectivity | |
|---|---|---|---|---|---|---|
| P(psig) | P(cmHg) | CO$_2$ | H$_2$ | CH$_4$ | CO$_2$/H$_2$ | CO$_2$/CH$_4$ |
| 20.7 | 60.3 | 0.0124 | 0.00686 | 0.00150 | 1.8 | 8.2 |
| 39.9 | 93.0 | 0.0118 | 0.00551 | nd | 2.1 | — |
| 60.4 | 128.0 | 0.0120 | 0.00645 | 0.00173 | 1.9 | 6.9 |
| 79.9 | 161.2 | 0.0112 | 0.00617 | 0.00210 | 1.8 | 5.3 | nd = none detected

EXAMPLE 9 SEPARATION OF A CO$_2$/CH$_4$/H$_2$ GASEOUS MIXTURE USING A MEMBRANE FORMED FROM A BLEND OF PVBTACl AND 1.0 EQUIV CsF

The active separating layer of facilitated transport membranes can be fabricated using water soluble polyelectrolytes which are unreactive with respect to acid gases by adding acid gas reactive salts such as CsF to such polyelectrolytes. A flat sheet PVBTACl-CsF membrane was prepared from an aqueous solution containing 3.99% PVBTACl and 1.0 equiv CsF. The permselectivity of the membrane was evaluated as a function of feed pressure under the conditions provided below.

PVBTACl-CsF flat sheet membranes at 23° C.; feed: 32.9% CO$_2$, 32.6% CH$_4$ in H$_2$; N$_2$ sweep; 5° C. feed and sweep water bubblers.

| feed | | $(P_i/l) \cdot 10^6$ cc/cm² · s · cmHg | | | selectivity | |
|---|---|---|---|---|---|---|
| P(psig) | P(cmHg) | $CO_2$ | $H_2$ | $CH_4$ | $CO_2/H_2$ | $CO_2/CH_4$ |
| 10.0 | 42.1 | 3.13 | 0.0896 | 0.00843 | 35 | 371 |
| 20.6 | 60.1 | 2.54 | 0.0808 | 0.00867 | 31 | 292 |
| 39.5 | 92.3 | 2.16 | 0.0893 | 0.00882 | 24 | 245 |

The $CO_2$ permeance of the membrane decreased with increasing feed pressure which is consistent with facilitated transport of the acid gas components of the test feedstream. In contrast, the PVBTACl membrane containing no salt (Example 8) exhibited low permeance and poor $CO_2/H_2$ and $CO_2/CH_4$ selectivities.

EXAMPLE 10 SEPARATION OF A $CO_2/CH_4/H_2$ GASEOUS MIXTURE USING A MEMBRANE FORMED FROM A BLEND OF PVBTACl AND $CsCH_3CO_2$

Example 10 provides facilitated transport membranes for separating acid gases wherein $CsCH_3CO_2$, a salt which is reactive with acid gas, is added to the separating layer of the membrane. A PVBTACl-$CsCH_3CO_2$ membrane was prepared from an aqueous solution containing 3.99% PVBTACl and 1.0 equiv $CsCH_3CO_2$. The permselectivity of the membrane was tested as a function of feed pressure under the conditions provided below.

PVBTACl-$CsCH_3CO_2$ flat sheet membranes at 23° C.; feed: 32.9% $CO_2$, 32.6% $CH_4$ in $H_2$; $N_2$ sweep; 5° C. feed and sweep water bubblers.

| feed | | $(P_i/l) \cdot 10^6$ cc/cm² · s · cmHg | | | selectivity | |
|---|---|---|---|---|---|---|
| P(psig) | P(cmHg) | $CO_2$ | $H_2$ | $CH_4$ | $CO_2/H_2$ | $CO_2/CH_4$ |
| 20.4 | 59.8 | 1.38 | 0.0928 | 0.00837 | 15 | 165 |
| 39.6 | 92.5 | 1.47 | 0.0994 | 0.00715 | 15 | 205 |
| 54.9 | 118.6 | 1.08 | 0.0907 | 0.00702 | 12 | 153 |

The $CO_2$ permeances of the membrane decreased with increasing feed pressure consistent with facilitated transport of the gas. In contrast, the PVBTACl membrane containing no salt (Example 8) exhibited low permeance and poor $CO_2/H_2$ and $CO_2/CH_4$ selectivities.

EXAMPLE 11 SEPARATION OF A $CO_2/CH_4/H_2$ GASEOUS MIXTURE USING A MEMBRANE FORMED FROM A BLEND OF PVOH and CsF Membranes were prepared using Vinol™125 PVOH homopolymer, available from Air Products and Chemicals, Inc., Allentown, Pa. A casting solution was prepared by slowly adding a 41.3% CsF aqueous solution to 3.94% PVOH resulting in a 3.1% polymer solution containing 0.9 equiv of CsF. Upon completing addition of the CsF solution to the homopolymer, a slight amount of polymer coagulation occurred. The coagulated polymer was removed by filtration. Permselective data was collected as a function of feed pressure under the conditions listed below.

PVOH-CsF flat sheet membrane at 23° C.; feed: 33.1% $CO_2$, 33.1% CH, in $H_2$; $N_2$ sweep; 5° C. feed and sweep water bubblers.

| feed | | $(P_i/l) \cdot 10^6$ cc/cm² · s · cmHg | | | selectivity | |
|---|---|---|---|---|---|---|
| P(psig) | P(cmHg) | $CO_2$ | $H_2$ | $CH_4$ | $CO_2/H_2$ | $CO_2/CH_4$ |
| 5.3 | 34.2 | 7.95 | 0.134 | nd | 59 | 300[a] |
| 20.0 | 59.5 | 7.15 | 0.136 | nd | 52 | 280[a] |
| 39.5 | 92.9 | 6.51 | 0.128 | 0.0254 | 51 | 256 |
| 58.8 | 126.0 | 5.99 | 0.260 | 0.110 | 23 | 56 |

[a]No $CH_4$ observed; selectivity based on observed $CH_4$ permeance of 0.0254.
nd = none detected A defect free PVOH membrane could not be obtained for comparative purposes, but it is well known that PVOH membranes exhibit low and relatively non-selective gas permeances.

EXAMPLES 12A and 12B SEPARATION OF A $CO_2/CH_4/H_2$ GASEOUS MIXTURE USING A MEMBRANE FORMED FROM A BLEND OF POLY(VINYLAMINE) AND CsF OR TMAF A membrane was prepared using a casting solution consisting of 1.62% PVAm and 0.92 equiv CsF. Permselective data was collected as a function of feed pressure under the conditions listed below. $CH_4$ was not detected in the permeate at the lower feed pressures examined. At the enumerated pressures, $CO_2/CH_4$ selectivities were estimated using the observed $CH_4$ permeance of 0.00686 at a feed pressure of 102.1 psig. A defect free membrane could not be prepared for comparative purposes, but the permselective properties of a PVAm membrane containing no added salt such membranes are expected to exhibit low and relatively non-selective gas permeances.

PVAm-0.9 CsF flat sheet membrane at 23° C.; feed: 33.1% $CO_2$, 33.1% $CH_4$ in $H_2$; $N_2$ sweep; 5° C. feed and sweep water bubblers.

| feed[a] | | $(P_i/l) \cdot 10^6$ cc/cm² · s · cmHg | | | selectivity | |
|---|---|---|---|---|---|---|
| P(psig) | P(cmHg) | $CO_2$ | $H_2$ | $CH_4$ | $CO_2/H_2$ | $CO_2/CH_4$ |
| 4.1 | 32.2 | 6.70 | 0.0556 | nd | 120 | 970[a] |
| 21.9 | 62.7 | 5.88 | 0.0514 | nd | 114 | 850[a] |
| 39.0 | 92.0 | 5.94 | 0.0566 | nd | 105 | 860[a] |
| 69.8 | 144.9 | 4.85 | 0.0516 | nd | 105 | 700[a] |
| 102.1 | 200.2 | 4.22 | 0.0428 | 0.00686 | 98 | 607 |

[a]estimated selectivity based on $CH_4$ permeance of 0.00686.
nd = none detected Somewhat lower permeances and selectivities were obtained for a membrane prepared from a casting solution consisting of 1.64% PVAm and 1.1 equiv TMAF. Experimental conditions are listed below.

PVAm-1.1 TMAF flat sheet membrane at 23° C.; feed: 33.1% $CO_2$, 33.1% $CH_4$ in $H_2$; $N_2$ sweep; 5° C. feed and sweep water bubblers.

| feed | | $CO_2$ | $(P_o/l) \cdot 10^6$ cc/cm² · s · cmHg | | | selectivity | |
|---|---|---|---|---|---|---|---|
| P(psig) | P(cmHg) | $CO_2$ | $H_2$ | $CH_4$ | $CO_2/H_2$ | $CO_2/CH_4$[a] (est. min.) | |
| 5.4 | 34.4 | 3.43 | 0.0727 | nd | 47 | 390 | |
| 39.9 | 93.6 | 3.18 | 0.0830 | nd | 39 | 360 | |
| 58.3 | 125.1 | 2.54 | 0.0839 | nd | 30 | 290 | |

[a]Estimated selectivity
nd = none detected $CH_4$ was not detected in the permeate over the entire range of feed pressures. Estimated minimum selectivities are based on a limit of detection of $CH_4$ of 25 ppm and the assumption that the $CH_4$ permeance is independent of pressure.

EXAMPLE 13 (COMPARATIVE) SEPARATION OF AN $H_2$S-CONTAINING GASEOUS MIXTURE USING A MEMBRANE FORMED FROM PVBTAF

A PVBTAF membrane was prepared as described in Example 1. Permselective data was collected as a function of feed pressure under the experimental conditions listed below. $CH_4$ was not detected in the permeate at the lower feed pressures examined. At the enumerated pressures, $CO_2/CH_4$ selectivities were estimated using an average observed $CH_4$ permeance of 0.0048.

PVBTAF flat sheet membrane at 22° C.; feed: 10.3% $H_2S$, 9.98% $CO_2$ in $CH_4$; helium sweep; 5° C. feed and sweep bubblers.

| feed | | $(P_o/l) \cdot 10^6$ cc/cm² · s · cmHg | | | selectivity | |
|---|---|---|---|---|---|---|
| P(psig) | P(cmHg) | $H_2S$ | $CO_2$ | $CH_4$ | $H_2S/CO_2$ | $H_2S/CH_4$ |
| 2.1 | 8.9 | 16.1 | 1.49 | nd | 10.8 | 3300[a] |
| 21.5 | 19.3 | 12.4 | 1.33 | nd | 8.5 | 2570[a] |
| 52.7 | 35.9 | 10.4 | 1.24 | nd | 8.4 | 2150[a] |
| 70.4 | 45.3 | 9.58 | 1.18 | 0.00530 | 8.1 | 1800 |
| 110.1 | 66.5 | 8.31 | 0.949 | 0.00436 | 8.7 | 1900 |

[a]Estimated selectivity.
nd = none detected

EXAMPLES 14 SEPARATION OF A $H_2$S-CONTAINING GASEOUS MIXTURE USING A MEMBRANE FORMED FROM A BLEND OF PVBTAF AND 0.5 EQUIV CsF

A flat sheet membrane was prepared on a microporous polysulfone support as described in Example 3 using an aqueous casting solution consisting of 3.98 wt. % PVBTAF and 1.1 equiv CsF. Permselective data was collected as a function of feed pressures under the experimental conditions listed below. Comparison with the performance at comparable $H_2S$ feed partial pressures of a PVBTAF membrane containing no salt (Example 13) shows that inclusion of CsF results in greater than twice the $H_2S$ permeance with minimal loss in selectivity.

PVBTAF-1.1CsF flat sheet membrane at 22° C.; feed: 9.94% $H_2S$, 10.0% $CO_2$ in $CH_4$;

helium sweep; 5° C. feed and sweep water bubblers.

| feed | | $(P_o/l) \cdot 10^6$ cc/cm² · s · cmHg | | | selectivity | |
|---|---|---|---|---|---|---|
| P(psig) | P(cmHg) | $H_2S$ | $CO_2$ | $CH_4$ | $H_2S/CO_2$ | $H_2S/CH_4$ |
| 20.6 | 18.1 | 33.2 | 6.77 | 0.0637 | 4.9 | 521 |
| 46.8 | 31.6 | 25.3 | 5.14 | 0.0550 | 4.9 | 460 |
| 70.9 | 44.0 | 23.2 | 4.06 | 0.0551 | 5.7 | 420 |
| 90.8 | 54.2 | 18.6 | 3.86 | 0.0509 | 4.8 | 364 |

EXAMPLES 15 SEPARATION OF A $H_2$S-CONTAINING GASEOUS MIXTURE USING A MEMBRANE FORMED FROM A BLEND OF PVBTAF AND 4.2 EQUIV CsF

A flat sheet membrane was prepared on a microporous polysulfone support using a casting solution consisting of 3.41 wt. % PVBTAF and 4.2 equiv CsF. Permselective data was collected as a function of feed pressures under the experimental conditions listed below. Over the entire range of feed pressures, $CH_4$ was not detected in the permeate. Comparison to the data in Example 14 for a PVBTAF membrane containing no acid gas reactive salt shows that inclusion of CsF results in a greater than five-fold increase in $H_2S$ permeance with equal or greater $H_2S/CH_4$ selectivities.

PVBTAF-4.2CsF flat sheet membrane at 30° C.; feed: 9.9% $H_2S$, 10.0% $CO_2$ in $CH_4$; helium sweep; 5° C. feed and sweep water bubblers.

| feed | | $(P_o/l) \cdot 10^6$ cc/cm² · s · cmHg | | | selectivity | |
|---|---|---|---|---|---|---|
| P (psig) | P (cmHg) | $H_2S$ | $CO_2$ | $CH_4$ | $H_2S/CO_2$ | $H_2S/CH_4$[a] (est. min.) |
| 1.1 | 8.1 | 91.6 | 8.91 | nd | 10.3 | 25000 |
| 25.7 | 20.8 | 73.6 | 8.83 | nd | 8.3 | 20000 |
| 35.4 | 25.7 | 57.3 | 8.30 | nd | 6.9 | 15600 |
| 50.2 | 33.3 | 42.0 | 9.03 | nd | 4.7 | 11400 |

[a]No $CH_4$ detected; based on maximum $CH_4$ permeance of 0.0037.
nd = none detected Estimated minimum $CO_2/CH_4$ selectivities were calculated based on a $CH_4$ limit of detection of 25 ppm and assuming that $CH_4$ permeance is independent of feed pressure.

EXAMPLES 16 SEPARATION OF A $H_2$S-CONTAINING GASEOUS MIXTURE USING A MEMBRANE FORMED FROM A BLEND OF PVBTAF AND 1.0 EQUIV CESIUM PIPECOLINATE

A flat sheet membrane was prepared using a casting solution consisting of 3.5% PVBTAF and 1.0 equiv cesium pipecolinate. Permselective data were collected as a function of feed pressures under the experimental conditions listed below.

PVBTAF-Cs(pipecolinate) flat sheet membrane at 22° C.; feed: 9.94% $H_2S$, 10.0% $CO_2$ in $CH_4$; helium sweep; 5° C. feed and sweep water bubblers.

| feed | | $(P_o/l) \cdot$ $10^6$ cc/cm$^2 \cdot$ s $\cdot$ cmHg | | | selectivity | |
|---|---|---|---|---|---|---|
| P(psig) | H$_2$S P(cmHg) | H$_2$S | CO$_2$ | CH$_4$ | H$_2$S/CO$_2$ | H$_2$S/CH$_4$ |
| 21.2 | 18.4 | 2.15 | 0.217 | 0.0180 | 9.9 | 120 |
| 53.8 | 35.2 | 1.05 | 0.151 | 0.0487 | 7.0 | 22 |
| 70.5 | 43.8 | 0.777 | 0.121 | 0.0430 | 6.4 | 18 |

EXAMPLE 17 SEPARATION OF A H$_2$S-CONTAINING GASEOUS MIXTURE USING A MEMBRANE FORMED A BLEND OF PVAm AND TMAF

A membrane was prepared using a casting solution consisting of 1.62% PVAm and 0.92 equiv TMAF. Permselective data were collected as a function of feed pressure under the conditions listed below. For none of the feed pressures examined was CH$_4$ observed in the permeate.

PVAm-TMAF flat sheet membrane at 30° C.; feed: 30.0% H$_2$S, 30.0% CO$_2$ in CH$_4$; helium sweep; 5° C. feed and sweep bubblers.

| feed | | $(P_o/l) \cdot$ $10^6$ cc/cm$^2 \cdot$ s $\cdot$ cmHg | | | selectivity | |
|---|---|---|---|---|---|---|
| P(psig) | H$_2$S P(cmHg) | H$_2$S | CO$_2$ | CH$_4$ | H$_2$S/CO$_2$ | H$_2$S/CH$_4$[a] (est. min.) |
| 5.4 | 31.2 | 56.4 | 4.14 | nd | 13.2 | 11000 |
| 20.3 | 54.4 | 44.5 | 3.53 | nd | 12.6 | 9000 |
| 40.4 | 85.6 | 27.4 | 2.81 | nd | 9.8 | 5500 |
| 63.0 | 120.7 | 22.7 | 2.62 | nd | 8.7 | 4600 |
| 93.6 | 168.3 | 9.4 | 1.80 | nd | 5.2 | 1900 |

[a]No CH$_4$ observed; based on calculated maximum CH$_4$ permeance of 0.0049.
nd = none detected Estimated minimum CO$_2$/CH$_4$ selectivities were calculated based on a CH$_4$ limit of detection of 25 ppm and assuming that CH$_4$ permeance is independent of feed pressure.

EXAMPLE 18 SEPARATION OF A CO$_2$/CH$_4$/H$_2$ GASEOUS MIXTURE USING A MEMBRANE FORMED FROM A BLEND OF PVBTAF AND 4.0 EQUIV. CHOLINE FLUORIDE (ChOHF)

A flat sheet membrane was prepared on a microporous polysulfone support using a methanolic casting solution consisting of 3.72 wt. % PVBTAF and 4.0 equiv HOCH$_2$CH$_2$N(CH$_3$)$_3$$^+$F$^-$ (ChOHF). Permselective data was collected as a function of the feed gas pressure under the conditions listed below.

PVBTAF-4.0 ChOHF flat sheet membrane at 23° C.; feed: 30.8% CO$_2$, 34% H$_2$, in CH$_4$; N$_2$ sweep; 5° C. feed and sweep water bubblers (nd=none detected).

| feed | | $(P_o/l) \cdot 10^6$ cc/cm$^2 \cdot$ s $\cdot$ cmHg | | | selectivity | |
|---|---|---|---|---|---|---|
| P(psig) | CO$_2$ P(cmHg) | CO$_2$ | H$_2$ | CH$_4$ | CO$_2$/H$_2$ | CO$_2$/CH$_4$ |
| 5.1 | 31.6 | 9.49 | 0.1392 | nd | 68 | — |
| 20.6 | 56.3 | 8.10 | 0.1551 | nd | 52 | — |
| 42.1 | 90.6 | 7.03 | 0.1625 | nd | 43 | — |
| 60.7 | 120.3 | 6.36 | 0.1941 | nd | 33 | — |

[a]Estimated selectivities
nd = none detected

The CO$_2$ permeances of this membrane are 1.5 fold greater than the PVBTAF membrane according to Example 1 wherein no acid gas reactive salt was added. The improved permeance is obtained without a significant loss in selectivity.

Example 19, presented below, demonstrates that the membranes of the present invention have utility as reversible acid gas absorbents. Any embodiment of the present invention is suitable for use in such applications for reversibly absorbing one or more acid gases as taught in this Specification.

EXAMPLE 19 POLYMER/SALT BLEND AS ACID GAS ABSORBENT REVERSIBLE ABSORPTION OF CO$_2$ BY MEMBRANE FORMED FROM BLEND OF PVBTAF AND CSF

An aqueous solution containing PVBTAF and 2.0 equiv CsF was evaporated to dryness under flowing N$_2$. A weighed quantity of the resulting solid was transferred into a stainless steel reactor at 23° C. Following evacuation, the sample was exposed to a known quantity and pressure of CO$_2$. The decrease in pressure due to absorption of CO$_2$ was monitored until no additional gas was absorbed and this pressure was used to calculate the quantity of CO$_2$ absorbed. Additional aliquots of gas were added to the reactor and absorption capacities were determined as above. Desorption data was obtained by removing a known quantity of gas from the system and allowing equilibrium to be reestablished. The quantities of CO$_2$ absorbed in terms of mole of CO$_2$ per mole of polymer repeat unit as a function of pressure are listed below. Since the water content of the sample was unknown, absorption capacities were calculated based on the assumption that the polymer-salt blend was anhydrous. Actual absorption quantities will be greater than those listed below since the sample certainly contained some bound water. As shown by the data, a blend consisting of PVBTAF-2.0 CsF exhibited large CO$_2$ absorption capacities. The data further shows that absorption was fully reversible and that gas was desorbed upon reducing the pressure of CO$_2$ above the sample.

| | Pressure CO$_2$ (kPa) | CO$_2$ absorption capacities (mole CO$_2$/mole polymer repeat unit) |
|---|---|---|
| Absorption data | 77.5 | 0.440 |
| | 134.1 | 0.477 |
| | 204.5 | 0.594 |
| Desorption data | 60.2 | 0.482 |
| | 19.6 | 0.379 |
| | 4.2 | 0.316 |
| | 3.6 | 0.259 |

The examples demonstrate that acid gas permeance of the composite membranes increases when an acid gas reactive salt of the enumerated compositions is blended with the water soluble polymer component of the active separating layer of the composite membrane. Applicant's process which utilizes a membrane having a separating layer formed from a water soluble polymer and an acid gas reactive salt provides substantially improved selectivity over the prior art facilitated transport membranes having a separating layer which does not contain the subject salts. Moreover, the improved selectivity is obtained without substantial losses in permeability and the feed stream is maintained at pressure.

Having thus described the present invention, what is now deemed appropriate for Letters Patent is set forth in the following Claims.

We claim:

1. A process for separating acid gas from a gaseous mixture containing acid gas and at least one non-acid gas, the process comprising contacting the gaseous mixture with a multilayer composite membrane comprising a first polymeric support layer and an active separating layer comprising a blend of a water soluble polymer and one-half equivalent or more of an acid gas reactive salt based upon the repeating unit of the water soluble polymer, the acid gas reactive salt which is represented by the formula $A_xB_y \cdot nH_2O$ wherein A is a monovalent cation and B is a monovalent anion wherein x and y are integers such that the salt remains charge neutral, n represents the number of moles of bound water per mole of salt, and the pKa of the conjugate acid of the monovalent anion is greater than 3, wherein the multilayer composite membrane separates the acid gas from the gaseous mixture by selectively permeating the acid gas.

2. The process of claim 1 wherein gaseous mixture contain water vapor in order to hydrate the acid gas reactive salt.

3. The process of claim 2 wherein the water soluble polymer of the separating layer of the composite membrane comprises a polyelectrolyte polymer.

4. The process of claim 3 wherein the polyelectrolyte polymer is selected from the group consisting of poly (vinylbenzyltrimethylammonium fluoride), poly (vinylbenzyltrimethylammonium chloride), poly (diallyldimethylammonium fluoride), poly (diallyldimethylammonium chloride), cesium poly(acrylate) and potassium poly(acrylate).

5. The process of claim 4 wherein the acid gas reactive salt of the active separating layer is selected from the group consisting of cesium fluoride, tetramethylammonium fluoride, cesium acetate, choline fluoride and cesium pipecolinate.

6. The process of claim 2 wherein the water soluble polymer of the active separating layer is a polymer which contains polar functional groups.

7. The process of claim 6 wherein the polymer which contains polar functional groups is selected from the group consisting of poly(vinyl alcohol), poly(vinyl amine) poly (ethyleneimine) and poly(ethylene oxide).

8. The process of claim 7 wherein the acid gas reactive salt of the active separating layer is selected from the group consisting of cesium fluoride, tetramethylammonium fluoride, cesium acetate, choline fluoride and cesium pipecolinate.

9. The process of claim 1 wherein the acid gas is selected from the group consisting of $CO_2$, $H_2S$, COS, $SO_2$, $NO_x$ and mixtures thereof.

10. The process of claim 1 wherein the non-acid gas component in the gaseous mixture is selected from the group consisting of hydrogen, methane, nitrogen, carbon monoxide and mixtures thereof.

11. The process of claim 1 wherein the first polymeric support layer is non-porous.

12. The process of claim 11 wherein the first non-porous polymeric support layer is selected from the group consisting of poly(dimethylsiloxane) and poly (trimethylsilylpropyne).

13. The process of claim 1 which further comprises sweeping the permeate side of the multilayer composite membrane with a sweeping gas to remove acid gas which are permeated by the membrane.

14. The process of claim 13 wherein the sweeping gas is an inert gas.

15. The process of claim 1 wherein the multilayer composite membrane is a three layer membrane wherein the separating layer is positioned between the first non-selective polymeric support layer and a second non-selective polymeric protective layer.

16. The process of claim 1 wherein the first polymeric support layer of the separating layer is porous.

17. The process of claim 16 wherein the pore size of the porous polymeric support layer is asymmetrically distributed.

18. The process of claim 1 wherein the gaseous mixture also contains water vapor which also permeates through the membrane.

19. The process of claim 1 wherein the water soluble polymer of the separating layer of the membrane comprises poly(vinylbenzyltrimethylammonium fluoride) and the acid gas reactive salt is selected from the group consisting of cesium fluoride, tetramethylammonium fluoride, cesium acetate and cesium pipecolinate.

20. The process of claim 1 wherein the water soluble polymer of the separating layer of the membrane comprises poly(vinylbenzyltrimethylaammonium chloride) and the acid gas reactive salt is selected from the group consisting of cesium fluoride and cesium acetate.

21. The process of claim 1 wherein the water soluble polymer of the separating layer of the membrane comprises poly(vinyl alcohol) and the acid gas reactive salt is selected from the group consisting of cesium fluoride and tetramethylammonium fluoride.

22. The process of claim 1 wherein the water soluble polymer of the active separating layer of the membrane comprises poly(vinyl amine) and the acid gas reactive salt is selected from the group consisting of cesium fluoride and tetramethylammonium fluoride.

23. The process of claim 1 wherein the composite membrane is configured as a flat sheet, a spiral wound membrane, a hollow fiber, or plate and frame configuration.

* * * * *